(12) United States Patent
Schohe-Loop et al.

(10) Patent No.: US 6,174,897 B1
(45) Date of Patent: Jan. 16, 2001

(54) BIS-(QUINOLYL)-DIAMINES

(75) Inventors: Rudolf Schohe-Loop, Wuppertal; Peter-Rudolf Seidel, Köln; William Bullock, Wuppertal; Achim Feurer, Odenthal; Georg Terstappen, Düsseldorf; Joachim Schuhmacher, Wuppertal; Franz-Josef van der Staay, Lohmar/Wahlscheid; Bernard Schmidt, Lindlar, all of (DE); Richard J. Fanelli, Madison, CT (US); Jane C. Chisholm, Clinton, CT (US); Richard T. McCarthy, Madison, CT (US)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/738,125

(22) Filed: Oct. 25, 1996

(51) Int. Cl.$^7$ .................. C07D 401/12; A61K 31/47
(52) U.S. Cl. .................. 514/312; 546/153; 546/156; 546/159; 546/160; 546/162; 546/163; 514/313
(58) Field of Search .................. 546/159, 153, 546/156, 160, 162, 163; 514/314, 312, 313

(56) References Cited

U.S. PATENT DOCUMENTS

| 3,026,322 | 3/1962 | Schock | 280/286 |
|---|---|---|---|
| 3,362,875 | 1/1968 | Strauss et al. | 167/58 |
| 3,974,279 | 8/1976 | Geiszler | 424/258 |

FOREIGN PATENT DOCUMENTS

| 1 246 733 | 9/1971 | (GB) . |
|---|---|---|
| WO 93/07126 | 4/1993 | (WO) . |
| WO 95/35287 | 12/1995 | (WO) . |

OTHER PUBLICATIONS

J.Med.Chem. 35(11), 1992, 2129–34.
J.Med.Chem. 14(4), 1971, 283–286.
Chem.Pharm.Bull. (1975), 23(8), 1869–73.
J.Med.Chem. 20(11), 1977, 1528–31.
Agr.Biol.Chem. (1971), 35(1), 119–21.
FEBS Lett. (1988), 228(2)235–40.
Mut.Res. (1990), 232(2), 337–43.
J.Med.Chem. 1996, 39, 359–370.
J.Org.Chem. 1994, 59, 5886–5890.
Sinha, et al., J. Med. Chem., 1977, 20(11), p. 1528.*
McFadgen et al, Chemical Abstracts vol. 113, entry 52145 (1990).*
McFadgen et al, Biochimica et Biophysic Acta, 1048 (1990) pp. 50–58.*
Singh, Chem. Pharm Bull 23(8) pp. 1869–1873 (1975).*
Deshpande et al, Agr. Biol. Chem., vol. 35, No. 1, pp. 118–121 (1971).*

* cited by examiner

*Primary Examiner*—John M. Ford
(74) *Attorney, Agent, or Firm*—Norris McLaughlin & Marcus P.A.

(57) ABSTRACT

The present invention relates to bis-(quinolyl)-diamines of the general formula (I):

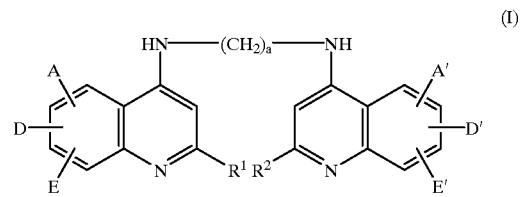

in which the indicated substituents are as defined in the description.

The invention also provides a process for the preparation of the compounds of the formula (I), their use for the preparation of drugs, and drugs containing said compounds.

3 Claims, No Drawings

BIS-(QUINOLYL)-DIAMINES

The present invention relates to novel bis-(quinolyl)-diamines, to processes for their preparation and to their use in drugs, especially as agents acting on the brain.

It is already known that N,N-bis-(7-chloroquinolin-4-yl)-alkanediamines are used as antimalarial drugs [cf. WO 95/35 287; J. Med. Chem. 35 (11), 1992, 2129–34; J. Med. Chem. 14 (4), 1971, 283–286; Chem. Pharm. Bull. 23 (8), 1975, 1869–73; PCT WO 93/07126].

Also, bis-quinaldines are know as drugs for topical infections and leukaemia, as monofunctional AT-selective DNA-intercalating agents and as antibacterial, antitubercular and antitumoral drugs [cf. J. Med. Chem. 20 (11), 1977, 1528–31; Agricultural and Biological Chemistry Vol. 35, 1971, 1, 119–21; FEBS Lett. 228 (2), 1988, 235–40; GB 12 46 733; U.S. Pat. Nos. 3,362,875; 3,974,279; Mutat. Res. 232 (2), 1990, 337–43; U.S. Pat. No. 3,026,322].

The publication J. Med. Chem. 1996, 39, 359–370, describes the synthesis and structure-activity relationship of dequalinium derivatives which are capable of inhibiting dequalinium-sensitive afterhyperpolarization.

The present invention relates to novel bis-(quinolyl)-diamines of the general formula (I):

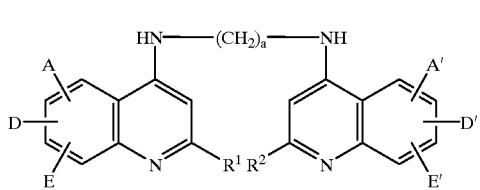

in which

A, A', D, D', E and E' are identical or different and are hydrogen, halogen, cycloalkyl having 3 to 8 carbon atoms, aryl having 6 to 10 carbon atoms, cyano, carboxyl, hydroxyl, linear or branched alkyl, alkoxy or alkoxycarbonyl, each of which has up to 8 carbon atoms, or a group of the formula —(CO)$_b$—NR$^3$R$^4$, wherein b is the number 0 or 1 and R$^3$ and R$^4$ are identical or different and are hydrogen or linear or branched alkyl having up to 5 carbon atoms, a is the number 2, 3, 4, 5, 6, 7 or 8, R$^1$ is linear or branched alkyl having 2 to 8 carbon atoms and R$^2$ is linear or branched alkyl having 1 to 8 carbon atoms or R$^1$ and/or R$^2$ are cycloalkyl having 3 to 8 carbon atoms or are phenyl which is optionally substituted by up to 3 identical or different substituents selected from halogen, hydroxyl, nitro, cyano, trifluoromethyl and linear or branched alkyl or alkoxy, each of which has up to 5 carbon atoms, and their salts.

Biocompatible salts are preferred within the framework of the present invention. Biocompatible salts of the novel bis-quinolyl)-diamines can be salts of the substances according to the invention with mineral acids, carboxylic acids or sulphonic acids. Examples of particularly preferred salts are those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

The compounds according to the invention can be present in different stereoisomeric forms within the framework of the present invention. The compounds according to the invention exist in stereoisomeric forms which either behave as image and mirror image (enantiomers) or do not behave as image and mirror image (diastereoisomers). The invention relates both to the antipodes and to the racemic forms and the diastereoisomeric mixtures. The racemic forms and the diastereoisomers can be resolved in known manner into the stereoisomerically pure components.

Preferred compounds of the general formula (I) according to the invention are those in which A, A', D, D', E and E' are identical or different and are hydrogen, fluorine, chlorine, bromine, cyclopropyl, cyclobutyl, cyclopentyl, cyclohexyl, phenyl, hydroxyl, linear or branched alkyl, alkoxy or alkoxycarbonyl, each of which has up to 7 carbon atoms, or a group of the formula —(CO)$_b$—NR$^3$R$^4$, wherein b is the number 0 or 1 and R$^3$ and R$^4$ are identical or different and are hydrogen or linear or branched alkyl having up to 4 carbon atoms, a is the number 2, 3, 4, 5, 6 or 7, R$^1$ is linear or branched alkyl having 2 to 7 carbon atoms and R$^2$ is linear or branched alkyl having 1 to 7 carbon atoms or R$^1$ and/or R$^2$ are cyclopropyl, cyclobutyl, cyclopentyl, cyclohexyl or cycloheptyl or are phenyl which is optionally substituted by fluorine, chlorine, bromine, hydroxyl or linear or branched alkyl or alkoxy, each of which has up to 3 carbon atoms, and their salts.

Particularly preferred compounds of the general formula (I) according to the invention are those in which A, A', D, D', E and E' are identical or different and are hydrogen, cyclopropyl, cyclopentyl, cyclobutyl, cyclohexyl, phenyl, hydroxyl, linear or branched alkyl or alkoxy, each of which has up to 3 carbon atoms, or a group of the formula —(CO)$_b$—NR$^3$R$^4$, wherein b is the number 0 or 1 and R$^3$ and R$^4$ are identical or different and are hydrogen or linear or branched alkyl having up to 3 carbon atoms, a is the number 2, 3, 4, 5 or 6, R$^1$ is linear or branched alkyl having 2 to 6 carbon atoms and R$^2$ is linear or branched alkyl having 1 to 6 carbon atoms or R$^1$ and/or R$^2$ are cyclopentyl or cyclohexyl or are phenyl which is optionally substituted by fluorine, chlorine, bromine or linear or branched alkyl or alkoxy, each of which has up to 3 carbon atoms, and their salts.

A process [A] for the preparanon of the compounds of the general formula (I) according to the invention has also been found, said process being characterized in that

[A] 2 equivalents of the compound of the general formula (II):

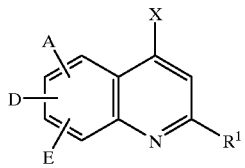

(II)

in which

A, D, E and $R^1$ are as defined above and

X is halogen, preferably fluorine or chlorine, are reacted with diamines of the general formula (III):

(III)

in which a is as defined above, optionally in inert solvents and optionally in the presence of a base and/or a iodine salt, or

[B] 1 equivalent of the compound of the general formula (II) is reacted in excess with the compounds of the general formula (III), under the conditions of process [A], to give compounds of the general formula (IV):

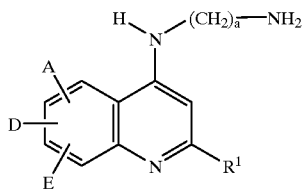

(IV)

in which

A, D, E and $R^1$ are as defined above, and these are then reacted with compounds of the general formula (IIa):

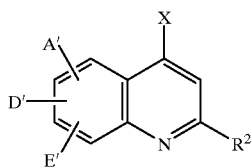

(IIa)

in which

A', D', E', $R^2$ and X are as defined above.

The process according to the invention can be exemplified by the following equation:

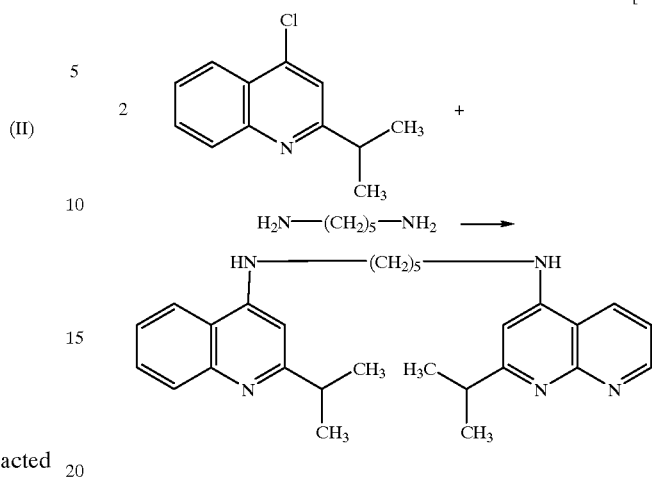

[A]

Suitable solvents are the conventional solvents which are not affected by the reaction conditions. These preferably include alcohols such as methanol, ethanol, propanol, isopropanol, hexanol, octanol or phenol, ethers such as diethyl ether, dioxane, tetrahydrofuran, glycol dimethyl ether or butyl methyl ether, ketones such as acetone or butanone, amides such as N-methylpyrrolidone, dimethlformamide or N-methylphosphorotriamide, dimethyl sulphoxide, acetonitrile, butyronitrile, ethyl acetate, halogenated hydrocarbons such as methylene chloride, chloroform or carbon tetrachloride, pyridine, picoline or N-methylpiperidine. It is also possible to use mixtures of said solvents. Butyronitrile, phenol and N-methylpyrrolidone are preferred. The reaction can also be carried out without a solvent.

Suitable bases are the conventional inorganic or organic bases. These preferably include alkali metal carbonates such as sodium or potassium carbonate, or organic amines such as diethylamine, triethylamine, tripropylamine, pyridine, picoline, N-methylpiperidine, lutidine or diisopropylethylamine. Diisopropylethylamine and tripropylamine are preferred.

Suitable iodine salts are alkali metal iodides such as lithium iodide, sodium iodide, potassium iodide and caesium iodide, and tetralkylammonium iodides such as benzyltributylammonium iodide. It is preferable to use sodium iodide and potassium iodide.

The iodine salts are generally used in an amount of 0.001 to 1 mol, based on 1 mol of the compounds of the general formula (II).

The base is used here in an amount of 0.8 to 5 mol, preferably of 0.8 to 2 mol, based on 1 mol of the compounds of the general formula (II).

The reactions are generally carried out in the temperature range between −20° C. and the reflux temperature of the solvent, preferably between +20° C. and the reflux temperature of the solvent.

The reaction can be carried out at normal, elevated or reduced pressure (e.g. 0.5 to 5 bar). It is generally carried out at normal pressure.

Some of the compounds of the general formula (II) are known or they can be prepared by known methods, for example by reacting 2-trifluoromethylaniline with ketones [cf. J. Org. Chem. 59, 1994, 5886].

The compounds of the general formula (III) are known per se or can be prepared by conventional methods.

The compounds of the general formulae (IV) and (IVa) are known or novel and can then be prepared as described above.

The compounds according to the invention possess a valuable pharmacological spectrum of action which could not be anticipated.

The compounds according to the invention are ligands for apamin-sensitive potassium channels. This can be shown by studying the affinity for apamin binding sites, e.g. in bovine cerebral membranes. The compounds according to the invention inhibit the ion flows through these channels, as can be shown by rubidium efflux experiments and with electrophysiological methods.

The compounds have a positive influence on learning and memory faculties, as demonstrated by their performance-enhancing action in typical learning and memory models like the water maze, the Morris maze, passive avoidance or reminiscence tests in automated Skinner boxes. They possess an antidepressant potential, as verified by their activity in the Porsolt rat swimming test.

The compounds according to the invention are also suitable for the treatment of myotonic dystrophy, alcoholism and other addiction diseases, sleep disturbances and bronchial asthma.

By virtue of their pharmacological properties, the compounds according to the invention can be used for the preparation of drugs for the treatment of degenerative diseases of the central nervous system, e.g. those occurring in cases of dementia (multi-infarct dementia, MID, primary degenerative dementia, PDD, presenile Alzheimer's disease, HIV dementia and other forms of dementia).

They are also suitable for the treatment of age-related cerebral faculty impairment, organic brain syndrome (OBS) and age-associated memory impairment (AAMI).

They are suitable for the treatment of depression and mania.

1) Binding of $^{125}$1I-apamine to Bovine Cerebral Membrane

Calf brains were obtained from the local abattoir. The hippocampus was prepared on ice and a membrane suspension was made up by homogenization twice in buffer (100 mM Tris-HCl, KCl 5 mM, pH 7.4) and centrifugation at 43,000×g. In a total volume of 500 µl, the incubation mixture contained 200 µg of membrane protein, 30 pM $^{125}$I-apamin and test substances in the concentration range $1\times10^{-9}$ to $1\times10^{-4}$ M. The non-specific binding of $^{125}$I-apamine was determined in the presence of $1\times10^{-7}$ M unlabelled apamin.

After preincubation for 30 min at room temperature (test substances and membrane homogenate), the samples were placed on ice for 10 min before the radioligand was added. The main incubation time was 60 min on ice. When the reaction time had elapsed, an excess of ice-cooled incubation buffer was added to each sample and the mixture was filtered with suction through cellulose acetate/nitrate membrane filters. The amount of bound $^{125}$I-apamin was measured with a gamma counter.

TABLE A

| Ex. no. | $K_i$ (nmol/l) |
|---|---|
| 1 | 17 |
| 2 | 13 |
| for comparison: | |
| J. Med. Chem. 39, 1996, 359 | |
| compound 2 | 2000 |
| compound 3 | 1000 |

Thus the compounds show an unexpectedly high affinity for apamin receptors in the calf brain.

2) Non-radioactive $Rb^+$Efflux Assay for the Identification of Potassium Channel Modulators The cellular potassium in PC12 cells is exchanged with rubidium, which is not present in the cells. This exchange is performed by incubating the cells over a period of 4 h in a physiological buffer containing 5.4 mM RbCl without KCl. This rubidium subsequently serves as a tracer for potassium. The cells laden with $Rb^+$in this way are washed three times and then stimulated by depolarization with 50 mM KCl to open potassium channels (10 min), causing $Rb^+$to flow out of the cells into the supernatant according to the concentration gradient.

The rubidium contents in the cell supernatant and in the residual cells after they have been lysed with 1% Triton X-100 are then determined by means of atomic absorption spectroscopy. The relative proportion of rubidium in the cell supernatent (=$Rb^+$efflux) is used as a measure of the potassium channel activity.

The effect of substances on the channel activity is measured by co-incubating the test substance over the ten-minute stimulation period and determining its effect on the $Rb^+$efflux in the manner described above.

TABLE B

| Ex. no | % inhibition of the Rb efflux at a test concentration of 10 µM |
|---|---|
| 1 | 77 |
| 4 | 75 (68% at 1 µM) |
| for comparison: | |
| J. Med. Chem. 39, 1996, 359 | |
| compound 2 | 45 (0% at 1 µM) |
| compound 3 | 28 |

Thus the compounds according to the invention show an unexpectedly high inhibitory activity on the apamin-sensitive rubidium efflux in PC12 cells.

3) Morris Maze

Male ICR mice, 6–8 wks old and approx. 22–28 g, were obtained from Harlan Sprague-Dawley, Inc. (Indianapolis, Ind.) and housed 8/cage with ad libitum access to food and water.

The behavioral apparatus consisted of a circular galvanized steel tank painted white with a diameter of 76 cm and divided into four equally spaced quadrants, each containing a plastic fitting that allowed for the placement of an escape platform. Prior to the start of the behavioral testing, the maze was filled daily to a depth of 1 cm above the escape platform (25 cm deep), maintained at a temperature of approx. 22° C., and was made opaque by the addition of 0.9 kg of powdered milk. Numerous stationary visual cues were present in the testing room. The data were recorded with the Multiple Zone Distance Traveled program of the Video-V analysis system (Columbus Instruments International Corp., Columbus, Ohio).

After a 1 week acclimatization to the animal facility, the mice were given a 90 sec free swim, during which no escape platform was present. One to three days later, acquisition training began and consisted of 4 trials on each day for a total of three days (12 total trials), during which no drugs were given. The mice were randomly assigned a goal quadrant in which the escape platform was located. Animals were then placed in the maze (facing away from the centre) at one of four equally spaced positions around the perimeter of the maze. The starting position varied for each mouse until they had started from each of the four positions once daily. On each of the training trials, the mice were allowed 120 sec to find the goal platform. If they failed to do so within the allotted time, they were placed on the platform. The intertrial interval was 30 sec, during which time the mouse remained on the platform.

On the fourth day, the mice were given a single 30 sec probe trial in which no escape platform was present. Thirty min or 1 hr prior to the start of the probe trial, mice were randomly assigned to groups that were given either drug or vehicle, and the time spent in each quadrant was measured.

The present invention also includes pharmaceutical formulations which contain one or more compounds of the general formula (I) together with inert, non-toxic, pharmaceutically appropriate adjuncts and excipients, or which consist of one or more active substances of the formula (I), as well as processes for the preparation of these formulations.

The active substances of the formula (I) should be present in these formulations in a concentration of 0.1 to 99.5% by weight, preferably of 0.5 to 95% by weight of the total mixture.

In addition to the active substances of the formula (I), the pharmaceutical formulations can also contain other pharmaceutical active substances.

The pharmaceutical formulations mentioned above can be prepared in conventional manner by known methods, for example with one or more adjuncts or excipients.

To achieve the desired result, it has generally proved advantageous to administer the active substance or substances of the formula (I) in total amounts of about 0.01 to about 100 mg/kg preferably in total amounts of about 0.01 mg/kg to 10 mg/kg of body weight per 24 hours, optionally in the form of several individual doses.

However, it may be advantageous to deviate from said amounts, depending on the nature and body weight of the subject treated, the individual response to the drug, the nature and severity of the disease, the type of formulation and administration and the time or interval at which the drug is administered.

General Working Instructions for the Preperation of the Bis-(quinolyl)-diamines

The appropriate 4-chloroquinoline derivative (20 mmol) and the diamine (20 mmol) were heated at 160° C. for 16 h under an argon atmosphere. After cooling to room temperature, 50 ml of 1 N sodium hydroxide solution and 100 ml of dichloromethane were added and the mixture was stirred until two homogeneous phases had formed. The organic phase was washed with water until the washings were neutral, dried over magnesium sulphate and concentrated to dryness. The product could be separated from the residue by column chromatography on aluminium oxide (ICN, type N, act. I) using dichloromethane/methanol/triethylamine 80/2/1 (unless indicated otherwise in the Tables) as the eluent. The product fractions were concentrated to dryness, taken up with 80 ml of dichloromethane and washed with 1 N sodium hydroxide solution (2×30 ml) and water (2×30 ml). The organic phase was dried over magnesium sulphate and concentrated to dryness to give the desired product. Extraction by stirring in a suitable solvent, e.g. tert-butyl methyl ether, was necessary for further purification in some cases.

Yield: 4–50%

The compounds listed in Table 1 were prepared in accordance with the above instructions:

TABLE 1

[Structure: Bis-quinolyl-diamine with HN—(CH$_2$)$_a$—NH linker, with substituents $R^1$, $R^2$ at the 2-positions and A, A' at the 8-positions of the two quinoline rings]

| Ex. No. | $R^1$ | $R^2$ | a | A | A' | M.p. |
|---|---|---|---|---|---|---|
| 1 | $C_2H_5$ | $C_2H_5$ | 5 | H | H | 160° C. |
| 2 | $(CH_2)_2CH_3$ | $(CH_2)_2CH_3$ | 5 | H | H | 165° C. |
| 3 | $CH(CH_3)_2$ | $CH(CH_3)_2$ | 5 | H | H | 168° C. |
| 4 | $CH(CH_3)_2$ | $CH(CH_3)_2$ | 5 | $CH_3$ | $CH_3$ | 168° C. |
| 5 | $CH(CH_3)_2$ | $CH(CH_3)_2$ | 3 | H | H | 198° C. |
| 6 | $CH(CH_3)_2$ | $CH_3$ | 5 | $CH_3$ | $CH_3$ | 72° C. |
| 7 | $CH(CH_3)_2$ | $CH(CH_3)_2$ | 5 | $CH_3$ | H | 152° C. |
| 8 | $C_6H_5$ | $C_6H_5$ | 5 | H | H | 86–88° C. |
| 9 | $CH(CH_3)C_2H_5$ | $CH(CH_3)C_2H_5$ | 5 | H | H | 202° C. |
| 10 | $CH(CH_3)_2$ | $CH(CH_3)_2$ | 5 | $CH(CH_3)_2$ | $CH(CH_3)_2$ | 108° C. |

Ex. no. M.p. (° C.)

We claim:

1. A method for treating dementias or depression which comprises administering to a patient in need thereof a pharmaceutically effective amount of a compound of the formula (I)

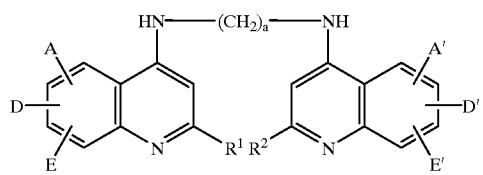
(I)

in which

A, A', D, D', E and E' are identical or different and are hydrogen, halogen, cycloalkyl having 3 to 8 carbon atoms, aryl having 6 to 10 carbon atoms, cyano, carboxyl, hydroxyl, linear or branched alkyl, alkoxy or alkoxycarbonyl, each of which has up to 8 carbon atoms, or a group of the formula —CO—$NR^3R^4$, wherein $R^3$ and $R^4$ are identical or different and are hydrogen or linear or branched alkyl having up to 5 carbon atoms, a is the number 2, 3, 4, 5, 6, 7 or 8, $R^1$ is linear or branched alkyl having 2 to 8 carbon atoms and $R^2$ is linear or branched alkyl having 1 to 8 carbon atoms or $R^1$ and $R^2$ are cycloalkyl having 3 to 8 carbon atoms or are phenyl which is optionally substituted by up to 3 identical or different substituents selected from halogen, hydroxyl, nitro, cyano, trifluoromethyl and linear or branched alkyl or alkoxy, each of which has up to 5 carbon atoms, and their salts.

2. A compound of the formula

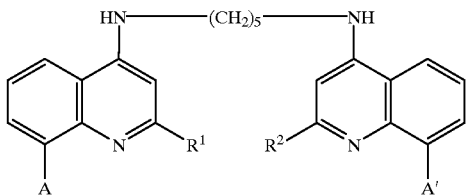

wherein $R^1$, $R^2$, a, A, and $A^1$ are selected from the following:

| $R^1$ | $R^2$ | a | A | $A^1$ |
|---|---|---|---|---|
| CH(CH$_3$)$_2$ | CH(CH$_3$)$_2$ | 5 | H | H |
| CH(CH$_3$)$_2$ | CH(CH$_3$)$_2$ | 5 | CH$_3$ | CH$_3$ |
| CH(CH$_3$)$_2$ | CH(CH$_3$)$_2$ | 3 | H | H. |

3. A pharmaceutical composition comprising at least one compound according to claim 2 and a biocompatible formulation aid.

* * * * *